United States Patent
Agha

(10) Patent No.: US 11,844,559 B2
(45) Date of Patent: *Dec. 19, 2023

(54) SURGICAL METHOD AND APPARATUS FOR DESTRUCTION AND REMOVAL OF INTRAPERITONEAL, VISCERAL, AND SUBCUTANEOUS FAT

(71) Applicant: Ayad K. M. Agha, Paradise Valley, AZ (US)

(72) Inventor: Ayad K. M. Agha, Paradise Valley, AZ (US)

( * ) Notice: Subject to any disclaimer, the term of this patent is extended or adjusted under 35 U.S.C. 154(b) by 800 days.

This patent is subject to a terminal disclaimer.

(21) Appl. No.: 16/840,363

(22) Filed: Apr. 4, 2020

(65) Prior Publication Data

US 2020/0246054 A1  Aug. 6, 2020

Related U.S. Application Data

(62) Division of application No. 16/266,037, filed on Feb. 2, 2019, now Pat. No. 10,610,280.

(51) Int. Cl.
*A61B 18/02* (2006.01)
*A61M 1/00* (2006.01)
*A61B 18/00* (2006.01)

(52) U.S. Cl.
CPC .... *A61B 18/02* (2013.01); *A61B 2018/00101* (2013.01); *A61B 2018/00464* (2013.01); *A61B 2018/00577* (2013.01); *A61B 2018/00982* (2013.01); *A61B 2018/0262* (2013.01); *A61B 2218/002* (2013.01); *A61M 1/84* (2021.05); *A61M 2202/08* (2013.01); *A61M 2205/05* (2013.01)

(58) Field of Classification Search
CPC .......... A61B 18/02; A61B 2018/00101; A61B 2018/00464; A61B 2018/00577; A61B 2018/00982; A61B 2018/0262; A61B 2218/002; A61M 2202/08; A61M 2205/05; A61M 1/008
USPC ........................................................ 604/542
See application file for complete search history.

(56) References Cited

U.S. PATENT DOCUMENTS

| | | | | |
|---|---|---|---|---|
| 4,946,460 A * | 8/1990 | Merry | ............ | A61B 18/02 606/24 |
| 6,032,675 A * | 3/2000 | Rubinsky | ............ | A61B 18/02 604/35 |
| 7,479,139 B2 * | 1/2009 | Cytron | ............ | A61B 18/02 606/20 |
| 10,610,280 B1 * | 4/2020 | Agha | ............ | A61B 18/02 |
| 2009/0118722 A1 * | 5/2009 | Ebbers | ............ | A61B 18/02 606/21 |

* cited by examiner

*Primary Examiner* — Andrew J Mensh
(74) *Attorney, Agent, or Firm* — Mark V. Loen

(57) ABSTRACT

The embodied invention is a method of removing intraperitoneal fat by using a freezing cryoprobe and inserting it into the abdominal cavity. The freezing cryoprobe is covered by a vacuum sleeve which provides for a method for abdominal fat removal once the cells are damaged. A multi-step surgical procedure is used to freeze, irrigate, and remove the destroyed fat tissue. Also, an ultrasonic transmitter is inserted into an outer cryoprobe sheath to assess organ position with the advantage of an internal transmitter which greatly aids in organ identification.

3 Claims, 10 Drawing Sheets

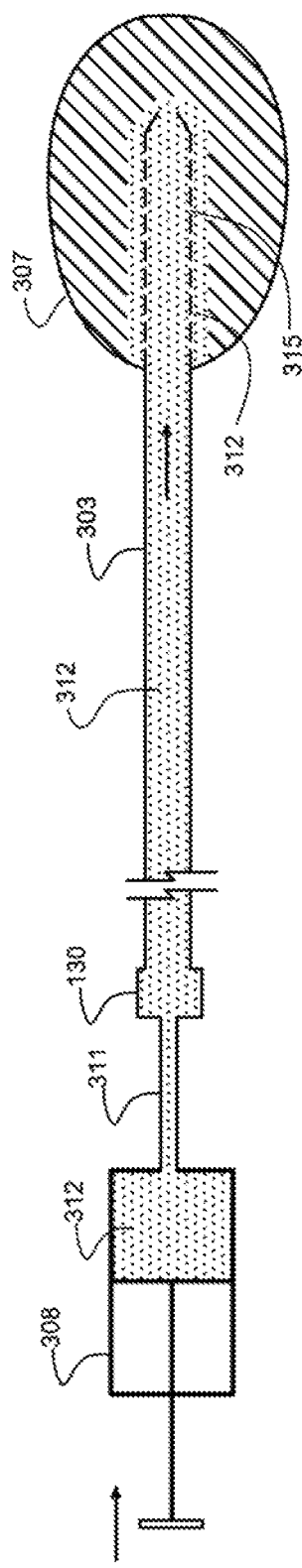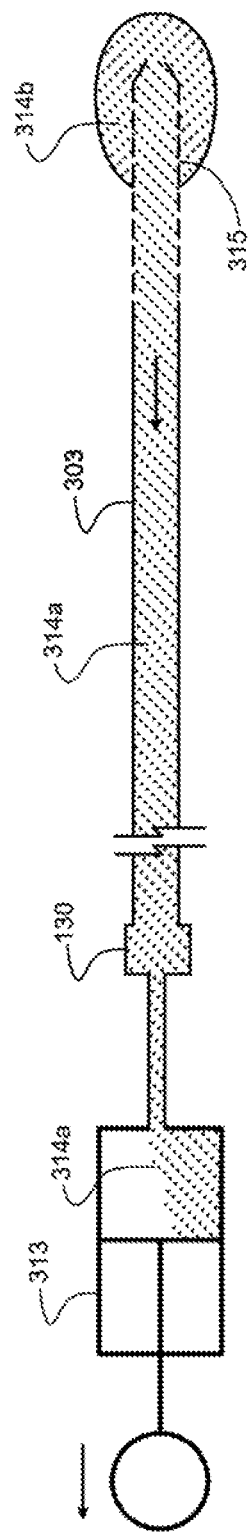

SURGICAL METHOD AND APPARATUS FOR DESTRUCTION AND REMOVAL OF INTRAPERITONEAL, VISCERAL, AND SUBCUTANEOUS FAT

CROSS REFERENCE TO RELATED APPLICATIONS

This application is a divisional application of U.S. application Ser. No. 16/266,037 filed on Feb. 2, 2019. The prior filed application is hereby incorporated by reference.

STATEMENT REGARDING FEDERALLY SPONSORED RESEARCH OR DEVELOPMENT

Not applicable.

REFERENCE TO SEQUENCE LISTING, A TABLE, OR COMPUTER PROGRAM LISTING

Not applicable.

BACKGROUND OF THE INVENTION

(1) Field of the Invention

This invention is directed to

(2) Description of Related Art

A study from the National Center for Health Statistics at the CDC showed that 39.6% of US adults age 20 and older were obese as of 2015-2016 (37.9% for men and 41.1% for women). Additionally, studies correlate heart attacks not just to being overweight, but to the amount of intraperitoneal fat (also called visceral fat).

Obesity in the United States is a major health issue, resulting in numerous diseases, specifically increased risk of certain types of cancer, coronary artery disease, type 2 diabetes, stroke, as well as significant economic costs.

If a surgical procedure to remove intraperitoneal fat could be developed there would be fewer heart attacks and improved health.

Currently, there is no surgical method available to remove intraperitoneal fat. The use of liposuction is not desirable as the process includes mechanical liquification of fat, which would damage internal organs.

Intraperitoneal fat is known to be difficult to remove by diet and exercise.

Cryosurgery is one method of killing tissue and is used for cancer treatments. It is a candidate for removal of intraperitoneal fat under the right conditions. However, current methods and equipment is inadequate to avoid internal organ damage when organs are interspersed in the intraperitoneal fat. Internal organs are likely to be damaged from freezing fat tissue if there is no methodology to identify organ positions to ensure that no damage is created. Additionally, current cryosurgery methods do not address removal of frozen tissue during surgery.

Others have worked in the field of cryogen treatments such as U.S. Pat. No. 6,041,787 where the system is described and its benefits. U.S. Pat. No. 5,531,742 describes computerized methods to monitor the frozen region and provide feedback to the surgeon.

U.S. Pat. No. 5,112,302 describes liposuction, which is used for removal of subcutaneous fat. The removal of fat is based on mechanical liquification of fat and then the fat is removed by vacuum. This motion of the cannula in the fat is very traumatic, and complications such as seromas, numbness, skin infections, or an internal puncture from the moving cannula can occur.

Cryosurgery is used in cancer treatment by utilizing liquid nitrogen or argon gas on cancerous tissue to destroy it. The gas is used to cool a cryoprobe which in turn is used to freeze an internal tumor and surrounding tissue. For an external tumor, liquid nitrogen is sprayed directly to the cancer cells or swabbed onto the tumor with a cotton swab.

There is need in the art for a way to surgically remove intraperitoneal and subcutaneous fat without damage to internal organs for improved health.

BRIEF SUMMARY OF THE INVENTION

The embodied invention is a method of removing intraperitoneal fat by using a cryoprobe and inserting it into the abdominal cavity. The cryoprobe is covered by a vacuum sleeve which provides for a method for intraperitoneal fat removal once the cells are damaged. A multi-step surgical procedure is used to freeze, irrigate, and remove the destroyed fat tissue. Also, an ultrasonic transmitter is inserted into an outer cryoprobe sheath to assess organ position with the advantage of an internal transmitter which greatly aids in organ identification.

BRIEF DESCRIPTION OF THE SEVERAL VIEWS OF THE DRAWING(S)

FIG. 3G-3K show the end of the cryoprobe and how it is used to create an ice ball of fat tissue, irrigate it, and remove it.

DETAILED DESCRIPTION OF THE INVENTION

When cryogenically treating cancer tumors inside the body, liquid nitrogen or argon flows through a hollow instrument called a cryoprobe, which is placed inside (or in contact with) the tumor to freeze it. Similarly, a cryoprobe can be used to freeze fat tissue.

In the embodied invention, a surgeon uses internal imaging equipment (ultrasound or MRI) to guide the cryoprobe to the correct location and monitor the freezing of the fat cells to avoid damage to nearby organs. When the cryogen (argon or nitrogen) cooled cryoprobe contacts the fat tissue, a ball of frozen tissue forms around the cryoprobe, killing the cells. The cryoprobe is put into the fat tissue through the skin (percutaneously). The frozen tissue is then thawed and removed. Sometimes, more than one freeze-thaw cycle is be used.

Figure 1:
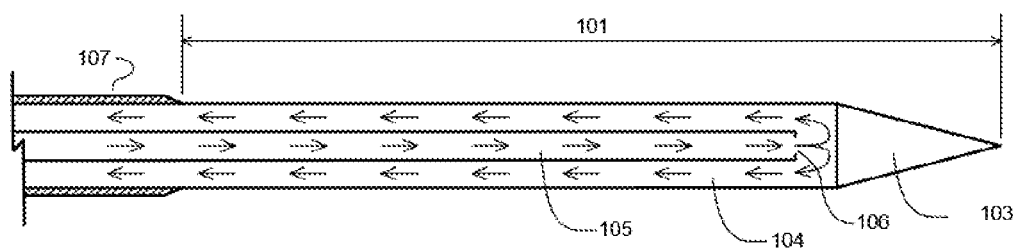
FIG. 1 shows a cross section of a cryogenic cryoprobe tip.

FIG. 1 (not to scale) is a cross section of the cryoprobe. The cryoprobe is typically 3-6 mm in diameter and the length 102 of the tip 103 is about 1.5 mm or so. The exposed tube length 101 is about 3-6 cm long. These dimensions are not strict requirements. The distal exposed section 101 of the cryoprobe is a cryocooler to reach the temperature needed to kill peritoneal fat cells. It is delineated by the insulation 107 along the length of the cryoprobe outer shaft. The insulation is preferably an insulating plastic.

The uninsulated length 101 is a cryocooler and freezes fat tissue from the cryoprobe surface outward. When the desired amount of tissue has been frozen, cryogen flow is stopped, and the tissue is allowed to thaw internally. When high pressure argon gas is used as the cryogen to cool the tip of the cryoprobe, it flows through a small diameter inner tube 105, and expands at the end of the inner tube 106. The expanding Argon gas cools the cryoprobe to a very low temperature due to the Joule-Thompson effect. The low pressure Argon gas is then routed through an exhaust chamber 104 to be vented away from the patient. No Argon gas is released inside the patient's body. U.S. Pat. Nos. 7,479,139 and 7,846,154 are examples of cryoprobes.

The term "high-pressure gas" refers to gas pressures that will cause a Joule-Thomson cooling of cryoprobes to −40° C. and lower. In the case of argon gas, for example, "high-pressure" argon is typically between 3000 psi and 4500 psi, though somewhat higher and lower pressures may be used. For a warming gas such as Helium, the working high pressure range is typically 1800-2500 psi.

Since freezing originates from the small uninsulated tip of the cryoprobe, cryosurgery can be confined to a small region of tissue, sparing the surrounding healthy tissue. The freezing process is precise and controlled, as the freezing interface in the fat tissue is sharp and propagates slowly from the tip. A small cryoprobe having a diameter of around 4 mm can produce a 3.5 cm diameter frozen ellipsoid ball to treat a relatively large tissue region in a few minutes. In general, cryosurgery does not create a lot of complications and has low patient morbidity. Cryosurgery produces excellent therapeutic results with less distress at a lower cost. In addition, retreatment is possible.

Figure 2A:
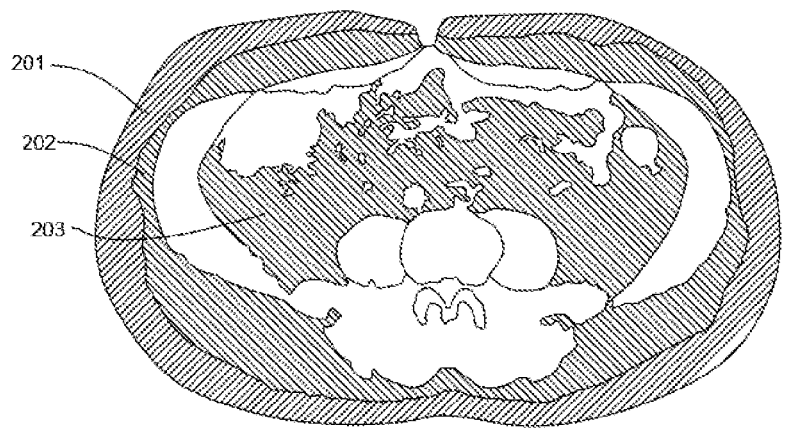
FIGS. 2A-2D show fat tissue in a horizontal cross section of a human abdomen, and placement of a cryoprobe.

FIG. 2A is a cross sectional image of abdominal fat tissue compartments. Fat tissues of specific areas are shown in cross hatching:
  201 subcutaneous fat,
  202 deep subcutaneous fat, and
  203 mesenteric visceral (intraperitoneal) fat.

Figure 2B:
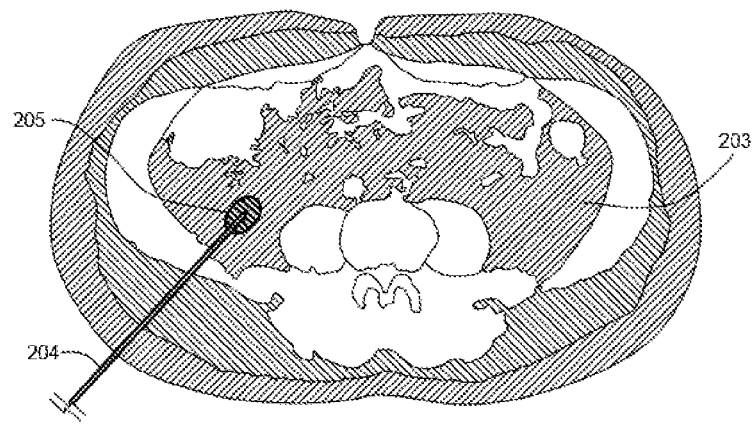

FIG. 2B shows a cryoprobe 204 inserted into the abdomen and creating an ice ball 205 of frozen intraperitoneal fat 203.

Figure 2C:
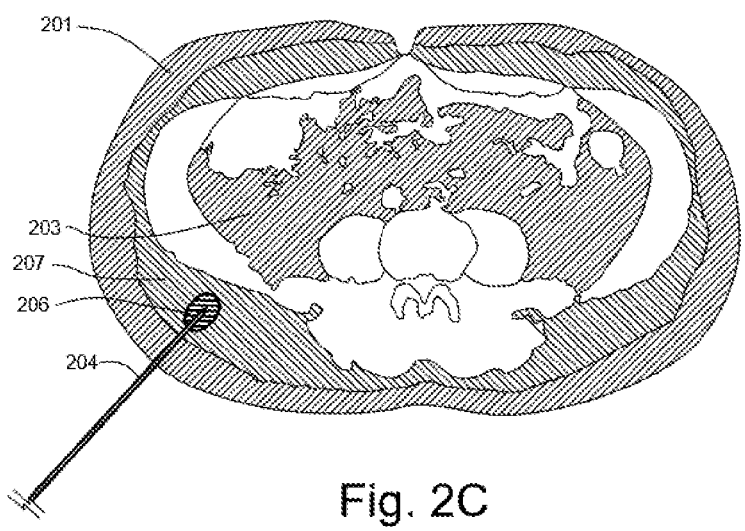
Figure 2D:
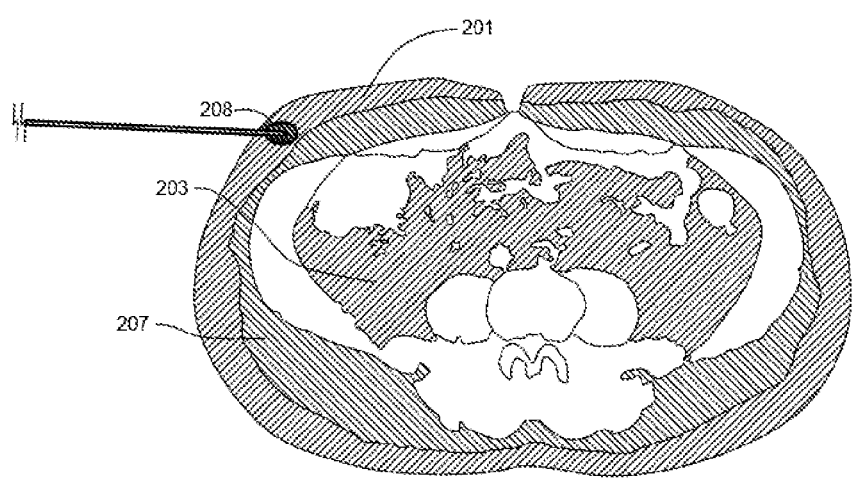

FIG. 2C shows a cryoprobe 204 inserted into the abdomen and creating an ice ball 206 of frozen retro-intraperitoneal fat 207. FIG. 2D shows a cryoprobe and an ice ball 208 of frozen subcutaneous fat.

Figure 4:
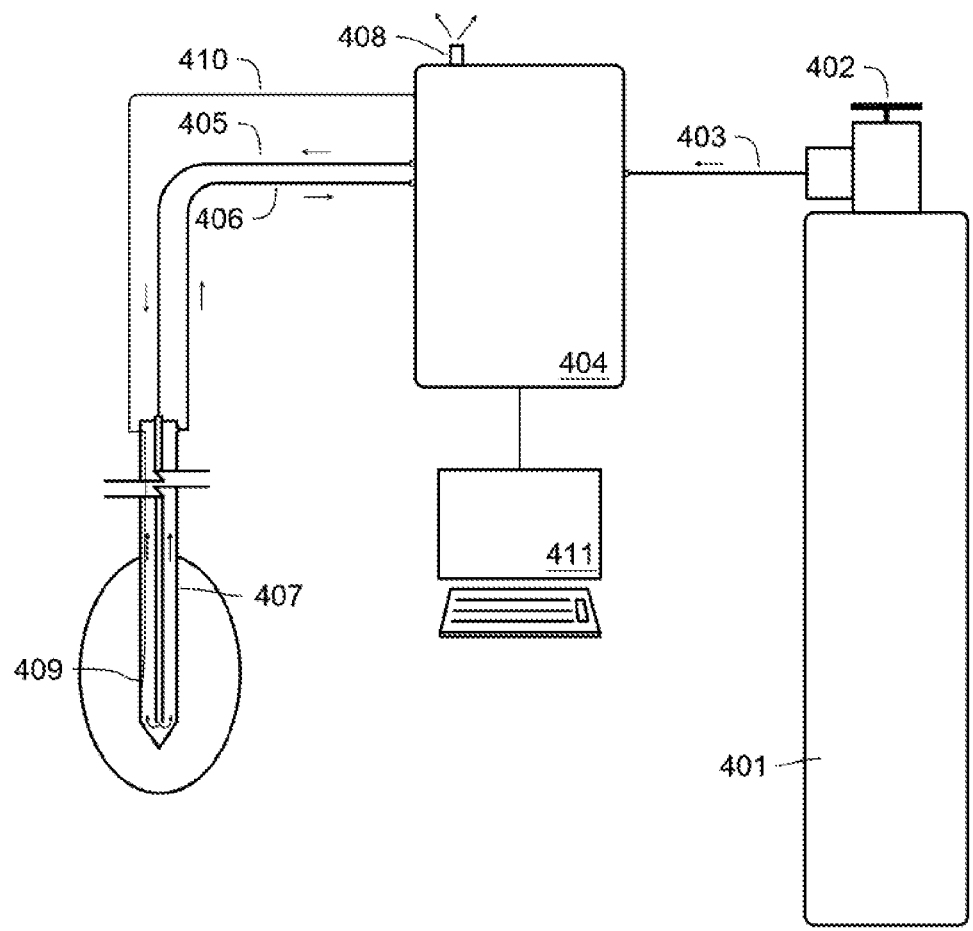
FIG. 4 shows how a cryogenic gas is connected to the cryoprobe.

In the surgical procedure, the Argon gas typically creates a cryoprobe end temperature of −40° C. for freezing fat tissue. However, only a temperature of −10° C. (or lower) is needed for cell destruction, and the cryoprobe end is alternately designed for less than −10° C. As shown in FIG. 4, Argon gas (or other cryogen gas) is supplied by a high pressure cylinder 401. A shutoff valve 402 on top of the cylinder is connected to a supply line 403 which is connected to a cryoprobe control system 404. The control system provides temperature regulation by regulating the amount of Argon allowed to a cryoprobe supply line 405. The return gas from the cryoprobe is routed through a return line 406 and is ultimately vented 408 from the cryoprobe control system. The control system includes needed piping and valve and automated computer control. A computer interface 411 provides for monitoring and operator supervisory control.

The cryoprobe temperature is monitored via a temperature sensor 409 located inside the cryoprobe tip, which is connected by a wire 410 to the control system 404. Thermal sensors include thermocouples and thermistor types.

Body heat will unfreeze the frozen fat ball (passive thawing) in about 6-12 minutes. In an alternate embodiment, helium is connected to the cryoprobe and operated to warm the cryoprobe for faster thawing (about 2-4 minutes). Helium properties are different than Argon, as it will heat, not cool, when expanded to atmospheric pressure. An alternate method of warming is to use radio frequency (RF). In this case the cryoprobe temperature measurement is used, and the radio frequency is adjusted to create the desired cryoprobe warming temperature. RF can also be used to increase the heat to a level that will stop any bleeding. Generally, heating tissue to a temperature of least 42° C. to 45° C. causes the irreversible cellular damage needed for thermal ablation.

Figure 5:
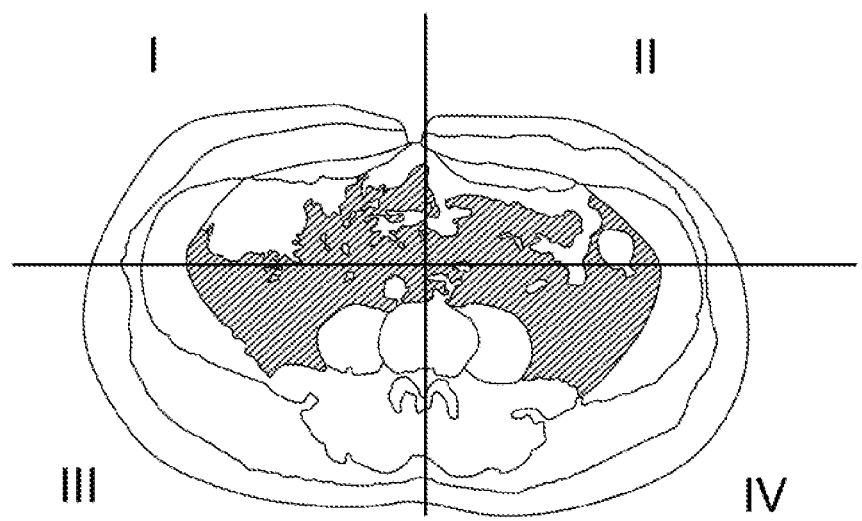
FIG. 5 shows how the abdomen is dived for repetitive treatments.

Multiple freezing sites can be done in a single surgical session. An efficient method is to divide the abdomen into quadrants as shown in FIG. 5. For example, the I and IV quadrants, and the II and III quadrants could be treated on different days, allowing for recovery between each surgical procedure. Alternately, the quadrants could be treated one at a time. It is preferable to treat two non-adjacent areas, i.e. (I & IV) or (II & III), at a time. To that end, the patient is preferably scanned (CT) to identify quadrant and organ dimensions, as well as how much visceral fat is removable.

The cryoprobe is either straight or curved. A curved cryoprobe is straight when inside the body, but some cryoprobes have a 90 degree bend outside of the body entry. The vacuum sleeve incorporates holes in the very end of the cryoprobe. The vacuum sleeve is preferably made from a surgical metal such as stainless steel. Alternately it could be made from a surgical plastic. The diameter of the cryoprobes is preferably 4 to 5 mm.

Figure 3A:
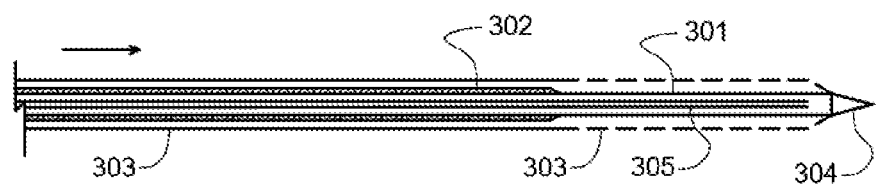
FIG. 3A-3F show the end of cryoprobe and how it is used in surgery.
Figure 3B:
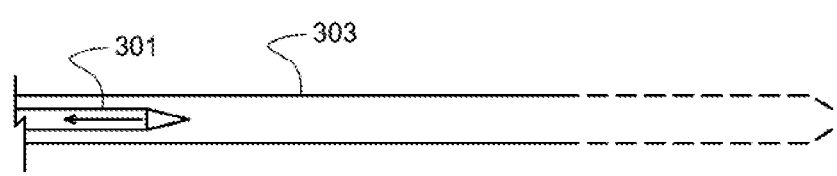
Figure 3C:
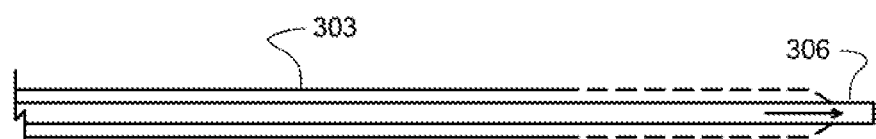
Figure 3D:
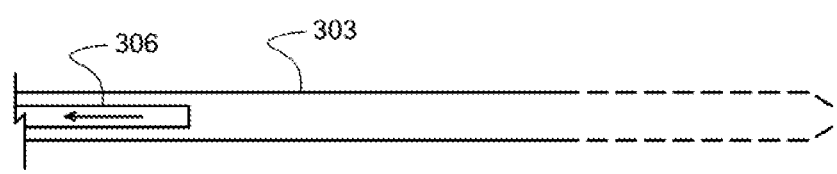
Figure 3E:
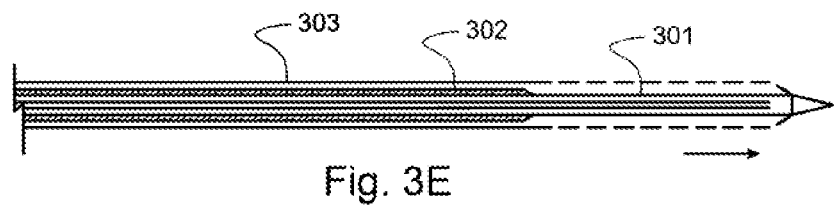
Figure 3F:
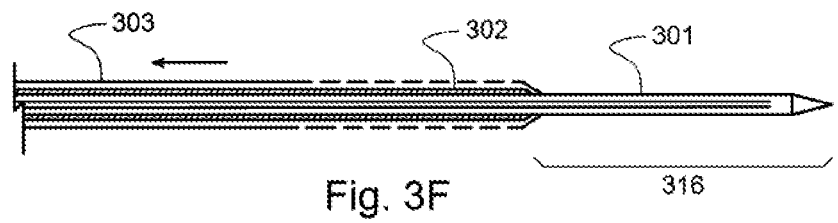
Figure 3G:
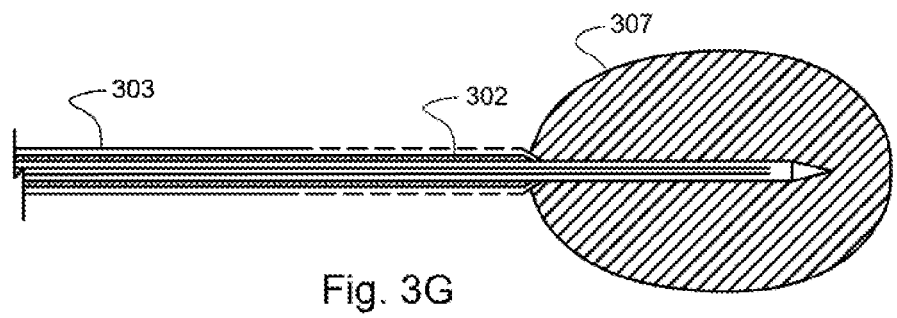
Figure 3H:
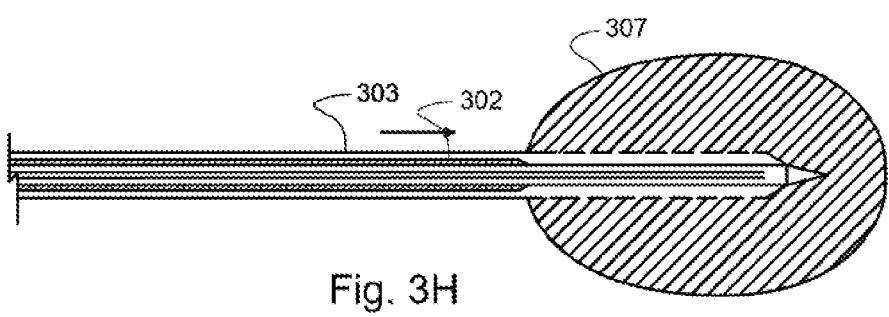
Figure 3I:
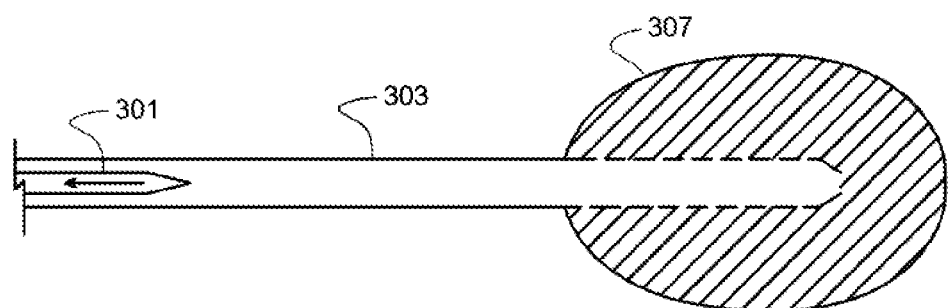

The surgical procedure comprises:
1. Create a small percutaneous incision for the cryoprobe to pass through.
2. FIG. 3A. Insert the cryoprobe and vacuum sleeve 303 as guided by an external ultrasound camera. Locate the cryoprobe tip 304 in a desired fatty tissue volume that will be removed. The cryoprobe includes outer an outer tubing 301, an outer insulation covering 302, an inner high pressure tubing 305, a penetration tip 304, and a temperature sensor/wire (not shown).
3. FIG. 3B. Remove the cryoprobe and leave the vacuum sleeve in place.
4. FIG. 3C. Insert an ultrasound transducer 306 into the vacuum sleeve and position at the end. Examine volume and position of fatty tissue. Determine how much cooling may be applied to the fatty tissue volume. Verify organ position with ultrasonic transducer/camera so that no organ tissue will be damaged. If needed, back out the vacuum sleeve and ultrasound transducer to avoid internal organs.
5. FIG. 3D. Withdraw the ultrasound transducer from the vacuum sleeve. The vacuum sleeve stays in the body.
6. FIG. 3E. Re-insert the cryoprobe into the vacuum sleeve to the previous cryoprobe position.
7. FIG. 3F. Withdraw the external sleeve 303 about 2-3 cm to reveal the cryoprobe tip so that an ice ball of frozen fat tissue can be made. The distal end 316 of the cryoprobe is the cryocooler.
8. Turn on the cryogenic control system and adjust the freezing cryoprobe temperature (about −40 to −50° C. to create the desired volume of frozen fat tissue (i.e. ice ball) 307. Monitor the freezing volume by using an external ultrasound camera. Turn off the cryogen flow when ice ball 307 freezing is completed.
9. FIG. 3H. Move the vacuum sleeve into the body to the previous position in step 5.
10. FIG. 3I. Completely withdraw the cryoprobe and leave the vacuum sleeve in place. The cryoprobe should easily separate from the ice ball.
11. FIG. 3J. Connect a cylinder/syringe 308 to a Leur Lock 130 using a connecting tubing 311. Push saline solution 312 into the vacuum sleeve 303 into the ice ball 307. Connect irrigation water (saline solution) 312 through the Leur Lock and vacuum sleeve into the ice ball 307. The end of the vacuum sleeve 303 has holes 315 that facilitate even irrigation coverage. Inject the desired amount of irrigation fluid into the freezing area to liquefy the frozen fat tissue. Disconnect the irrigation fluid from the external sleeve.
12. FIG. 3K. Connect an evacuating syringe 313 to the Leur Lock 130 and apply a vacuum to remove the liquified frozen volume 134*a,b*. Monitor the removal area using an external ultrasound camera. Oscillate the external sleeve in and out of the abdomen slightly to aid in removal of liquified fat tissue.
13. When all of the desired liquified fat tissue has been removed, withdraw the vacuum sleeve.
14. Inspect and close the skin opening. The opening in the skin is covered with a bandage. Sutures are applied if needed.

Imaging is preferably done with an ultrasound transducer operating at 12 megahertz. The ultrasound transducer optionally incorporates an imaging sensor to receive the image signals. Typically, a surgeon will be able to see about 4-10 cm depth around the ultrasound cryoprobe. The preferred method for imaging is ultrasound because it is more mobile and radiation free. X-Ray imaging (CT Scan) is not preferred as it emits radiation, and is a large, immobile machine.

Cryosurgery does not require any special patient preparation. It is important that the patient does not eat prior to surgery for four hours due to being sedated.

As a quality check, and before use, the cryoprobe is checked by inserting it into sterile water and a cold temperature created by utilizing the cryogen gas for cooling. If a normal ice ball occurs in the water without leaking Argon, it is ready to be used.

Argon is the preferred cryogen, but Nitrogen (gas or liquid) may also be used.

There is no particular limitation to amount of procedures that can be performed to remove fatty tissue.

To aid in pain control, lidocaine is used to numb the insertion area.

In an additional embodiment, the irrigating solution includes lidocaine for numbing and epinephrine for blood clotting. In an exemplary embodiment, the irrigating solution is a mixture of:
1. 400 ml saline solution (sterile water and 0.9% by weight NaCl),
2. 10 ml sodium bicarbonate-buffer (about 8.4% by weight), and
3. 50 ml of water with
   a. 0.05% lidocaine by volume, and
   b. epinephrine at 1:1,000,000 by volume.

The amount of the irrigating mixture used for irritation is as needed.

Fat tissues of specific anatomical landmarks are divided into areas and shown in FIGS. 2A-2B as follows:

1. subcutaneous fat 201,
2. deep subcutaneous fat 202, and
3. intraperitoneal visceral fat 203, and
4. other non-shaded tissue and vertebrae.

In FIG. 4, a simplified schematic of the cryogen supply and control system 404 is shown. A high pressure Argon gas cylinder 401 connects to a cylinder supply valve 402. A supply line 403 connects the cylinder to a system controller 404. A supply line 405 and return line 406 connect to the cryoprobe 407. An internal temperature sensor 409 connects to the control system with a connecting wire 410. Spent Argon is released through a vent 408. A surgeon computer interface 411 to the control system 404 allows the surgeon to monitor and control the cryoprobe freezing.

Figure 6:
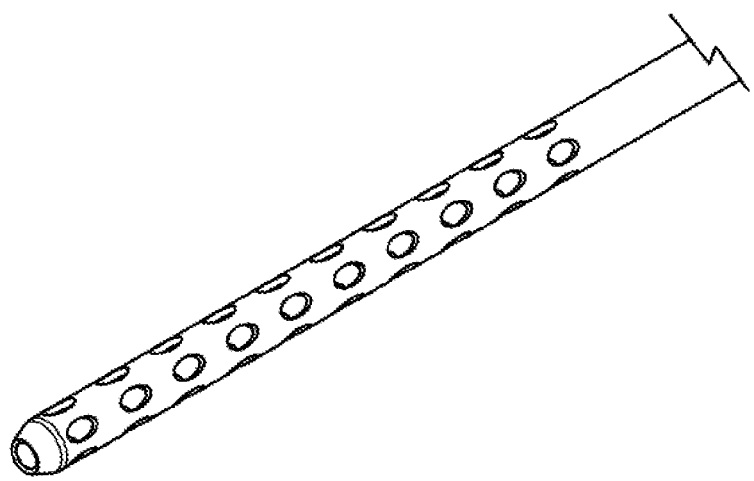
FIG. 6 is a perspective view of the vacuum sleeve, illustrating the end holes.

FIG. 6 is a perspective view of the vacuum sleeve, illustrating the perforated holes at the distal end of the vacuum sleeve. The holes are either an evenly geometric pattern, as illustrated, or a random pattern. The holes are generally conceived to be either elliptical or circular. In one embodiment of the invention, the holes are about 3 mm in diameter, with centers spaced about 10 mm apart. However, this is not strict requirement.

It is important that a specially trained physician performs the surgical procedure. Preferably it is done on an outpatient basis. The surgical procedure begins when the cryogenic equipment is ready, and the cryoprobe has been confirmed to be functional.

During the procedure, the patient is connected to monitors that track heart rate, blood pressure, and pulse. The area where the applicators or cryoprobe are to be inserted will be shaved, sterilized, and covered with a sterile drape.

The surgeon only needs to make a very small skin incision is made at the site. The surgeon then performs a percutaneous procedure and inserts the thin, needle-size cryoprobes.

In a preferred embodiment, aside from the cryoprobe(s), transducer, irrigating fluid, and vacuum sleeve, nothing else enters the body.

The entire procedure will only take one to three hours.

In an alternate embodiment, RF warming is used to free up any sticking of the cryoprobe. A different cryoprobe (not illustrated) is used that is capable of RF heating.

The computer is capable of communicating with a temperature sensor and utilizing the temperature sensor for control. Additionally, the computer receives the ultrasound transducer output signal and interprets it into a visual image. The computer may be a desktop computer, a lap top computer, a server, a workstation, a handheld computer, a tablet computer, a single board computer, etc. Preferably the computer is in near proximity to the cryogenic supply unit and integrated into the equipment as shown in FIG. 4.

As used herein the terms central computer or computer system are intended to refer to a computer-related entity, comprising either hardware, a combination of hardware and software, software, or software in execution capable of performing the embodiments described. The disclosed embodiments which use the central computer refer to being interfaced to and controlled by a computer readable storage medium having stored thereon a computer program. The computer readable storage medium may include a plurality of components such as one or more of electronic components, hardware components, and/or computer software components. These components may include one or more computer readable storage media that generally store instructions such as software, firmware and/or assembly language for performing one or more portions of one or more implementations or embodiments of an algorithm as discussed herein. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or solid-state or electronic memory. Other forms of non-transitory and/or tangible computer readable storage media not list may be employed with the disclosed embodiments.

A number of such components can be combined or divided in an implementation of a computer system. Further, such components may include a set and/or series of computer instructions written in or implemented with any of a number of programming languages, as will be appreciated by those skilled in the art. Computer instructions are executed by at least one central processing unit. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

While various embodiments of the present invention have been described, the invention may be modified and adapted to various operational methods to those skilled in the art. Therefore, this invention is not limited to the description and figure shown herein, and includes all such embodiments, changes, and modifications that are encompassed by the scope of the claims.

I claim:

1. An apparatus for removing intraperitoneal fat and identifying a correct position of a cryoprobe comprising:
   A) a cryoprobe further comprising:
      a) an insulated cryoprobe tube with a closed distal operating tip,
      b) said distal operating tip is non-insulated,
      c) said distal operating tip comprises a cryocooler operable to cool to cryoablation temperatures of said intraperitoneal fat surrounding said distal operating tip,
      d) said cryoprobe tube incorporates a coaxial cryogen exhaust chamber for exhausting cold cryogen from said cryocooler, and
      e) a coaxial cryogen gas delivery tube inside said cryoprobe tube;
   B) an outer vacuum sleeve incorporating a plurality of perforations at a distal end, wherein said outer vacuum sleeve is coaxial to said cryoprobe and operable to move relative to said cryoprobe; and
   C) an ultrasonic transmitter configured to fit coaxially inside said outer vacuum sleeve and move relative to said outer vacuum sleeve;
   wherein said cryoprobe also configured to fit coaxially inside said outer vacuum sleeve and operable move relative to said outer vacuum sleeve;
   said outer vacuum sleeve configured to sequentially place said ultrasonic transmitter and said cryoprobe inside an abdomen according to a surgical procedure;
   said ultrasonic transmitter configured to determine internal organ positions;
   said cryoprobe configured to freeze said intraperitoneal fat according to said surgical procedure;
   said cryoprobe and said ultrasonic transmitters configured to be withdrawn according to said surgical procedure;
   said outer vacuum sleeve configured to irrigate and remove decomposed said intraperitoneal fat; and
   whereby said apparatus is operable to remove said intraperitoneal fat without internal organ damage when performing said surgical procedure.

2. The apparatus according to claim 1, wherein:
   said plurality of perforations are arranged in a geometric pattern or a random pattern, and
   said perforations are 3 mm in diameter with centers spaced 10 mm apart.

3. The apparatus according to claim 1, wherein said internal imaging equipment comprises an ultrasound sensor and a display.

* * * * *